United States Patent
Maekawa et al.

(10) Patent No.: US 9,950,929 B2
(45) Date of Patent: Apr. 24, 2018

(54) METHOD FOR PRODUCING DISULFONYLAMINE ALKALI METAL SALT

(71) Applicant: NIPPON SODA CO., LTD., Tokyo (JP)

(72) Inventors: Hideki Maekawa, Joetsu (JP); Masamichi Yasuhara, Myoukou (JP); Ken-ichi Hayashi, Joetsu (JP)

(73) Assignee: NIPPON SODA CO., LTD., Tokyo (JP)

( * ) Notice: Subject to any disclaimer, the term of this patent is extended or adjusted under 35 U.S.C. 154(b) by 219 days.

(21) Appl. No.: 14/773,964

(22) PCT Filed: Mar. 5, 2014

(86) PCT No.: PCT/JP2014/055622
§ 371 (c)(1),
(2) Date: Sep. 9, 2015

(87) PCT Pub. No.: WO2014/148258
PCT Pub. Date: Sep. 25, 2014

(65) Prior Publication Data
US 2016/0016797 A1  Jan. 21, 2016

(30) Foreign Application Priority Data
Mar. 18, 2013  (JP) .................. 2013-055571

(51) Int. Cl.
| C01B 21/086 | (2006.01) |
| C07C 303/40 | (2006.01) |
| C07C 311/48 | (2006.01) |
| H01M 10/0525 | (2010.01) |
| H01M 10/0568 | (2010.01) |

(52) U.S. Cl.
CPC .......... *C01B 21/086* (2013.01); *C07C 303/40* (2013.01); *C07C 311/48* (2013.01); *H01M 10/0525* (2013.01); *H01M 10/0568* (2013.01)

(58) Field of Classification Search
CPC .................................................. C01B 21/086
See application file for complete search history.

(56) References Cited

U.S. PATENT DOCUMENTS

| 5,916,475 A | 6/1999 | Michot et al. |
| 2010/0331321 A1 | 12/2010 | Bylund et al. |
| 2012/0041233 A1 | 2/2012 | Sato et al. |
| 2013/0068991 A1 | 3/2013 | Sato et al. |
| 2013/0323154 A1 | 12/2013 | Tsubokura et al. |
| 2013/0323155 A1 * | 12/2013 | Tsubokura ............ C07C 303/40 423/386 |
| 2013/0331609 A1 | 12/2013 | Tsubokura et al. |

FOREIGN PATENT DOCUMENTS

| CN | 101945859 A | 1/2011 |
| JP | 8-511274 A | 11/1996 |
| JP | 2000-86617 | * 3/2000 |
| JP | 2000-86617 A | 3/2000 |
| JP | 2003-192661 | * 7/2003 |
| JP | 2003-192661 A | 7/2003 |
| JP | 2010-168249 A | 8/2010 |
| WO | 2009/123328 A1 | 10/2009 |
| WO | 2009/132241 A2 | 10/2009 |
| WO | 2011/065502 A1 | 6/2011 |
| WO | 2011/149095 A1 | 12/2011 |
| WO | 2012/108284 A1 | 8/2012 |
| WO | 2012/117961 A1 | 9/2012 |

OTHER PUBLICATIONS

Office Action dated Jul. 5, 2016, issued in counterpart Chinese Application No. 201480014935.3, with English translation (8 pages).
International Search Report dated Jun. 10, 2014, issued in counterpart International Application No. PCT/JP2014/055622 (4 pages).
Third Party Observation dated Jul. 8, 2015, issued in counterpart International Application No. PCT/JP2014/055622 (9 pages).
Matsuda et al., "Effects of Electrolyte Imide Salt Purity on Negative Electrode Charge-Discharge Characteristics in Lithium Secondary Cells", Proceedings of the 68th Conference of the Electrochemical Society of Japan, Mar. 25, 2001, pp. 232, w/ English translation.
General catalogue 2013/2014, Laboratory Equipment & Instruments Filtration Media & Filtration System, cited in the Third Party Observation, w/ partial English translation (16 pages).

* cited by examiner

*Primary Examiner* — Wayne Langel
(74) *Attorney, Agent, or Firm* — Westerman, Hattori, Daniels & Adrian, LLP

(57) ABSTRACT

The present invention provides a method for producing a disulfonylamine alkali metal salt, including a step of subjecting a disulfonylamine onium salt represented by formula [I] (wherein each of $R^1$ and $R^2$ independently represents a fluorine atom or a fluorinated alkyl group having 1 to 6 carbon atoms, provided that at least one of $R^1$ and $R^2$ represents a fluorine atom, and each of $R^3$, $R^4$, $R^5$ and $R^6$ independently represents a hydrogen atom or the like) to a cation exchange reaction in an organic solvent, thereby producing a disulfonylamine alkali metal salt represented by formula [II] (wherein $M^+$ represents an alkali metal cation, and $R^1$ and $R^2$ are as defined in formula [I]), and a step of filtering the organic solvent solution containing the disulfonylamine alkali metal salt through a filter having a particle retention size of 0.1 to 10 μm to obtain a filtrate.

[Chemical Formula 1]

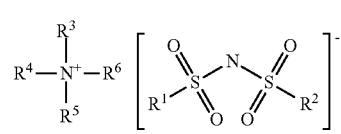

[Chemical Formula 2]

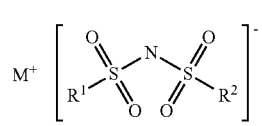

3 Claims, No Drawings

METHOD FOR PRODUCING DISULFONYLAMINE ALKALI METAL SALT

TECHNICAL FIELD

The present invention relates to a method for producing a disulfonylamine alkali metal salt. More specifically, the present invention relates to a method for producing a high-purity disulfonylamine alkali metal salt with a low temperature history and at low cost.

Priority is claimed on Japanese Patent Application No. 2013-055571, filed Mar. 18, 2013, the content of which is incorporated herein by reference.

BACKGROUND ART

Disulfonylamine alkali metal salts are compounds that are useful as electrolytes for secondary cells or as additives for adding to electrolytes of secondary cells (Patent Document 1). Further, it is known that reducing the amount of impurities within the electrolyte of a secondary cell has a favorable effect on the discharge capacity and the current efficiency of charging and discharging the secondary cell (Non-Patent Document 1). Accordingly, the development of methods for producing disulfonylamine alkali metal salts with high purity are currently being pursued.

For example, Patent Document 2 proposes a method for producing a high-purity disulfonylamine salt in which following the fluorination reaction of bis(chlorosulfonyl)amine, the reaction solution is brought into contact with an aqueous alkaline solution in order to remove impurities.

Patent Document 3 proposes a method for producing a disulfonylamine alkali metal salt which includes a step of concentrating a solution of the disulfonylamine alkali metal salt while bubbling a gas through the reaction solution that contains the disulfonylamine alkali metal salt, and/or a step of concentrating a solution of the disulfonylamine alkali metal salt by thin-film distillation.

Patent Document 4 proposes a method for producing a bis(fluorosulfonyl)amine alkali metal salt by reacting a bis(chlorosulfonyl)amine ammonium salt with hydrogen fluoride to obtain a bis(fluorosulfonyl)amine ammonium salt, and then reacting an alkali metal compound or the like with the obtained bis(fluorosulfonyl)amine ammonium salt.

PRIOR ART LITERATURE

Patent Documents

Patent Document 1: JP H08-511274 A
Patent Document 2: WO2011/065502
Patent Document 3: WO2011/149095
Patent Document 4: WO2012/108284

Non-Patent Documents

Non-Patent Document 1: Yoshiharu Matsuda et al., Effects of Electrolyte Imide Salt Purity on Negative Electrode Charge-Discharge Characteristics in Lithium Secondary Cells, Proceedings of the 68th Conference of The Electrochemical Society of Japan, Mar. 25, 2001, page 232.

DISCLOSURE OF INVENTION

Problems to be Solved by the Invention

In the methods disclosed in Patent Documents 2 and 4, a high-purity disulfonylamine alkali metal salt is sometimes unobtainable. The method disclosed in Patent Document 3 requires special equipment, and includes a high temperature history during the thin-film distillation, and therefore the production costs tend to be high.

Accordingly, an object of the present invention is to provide a method for producing a high-purity disulfonylamine alkali metal salt with a low temperature history and at low cost.

Means for Solving the Problems

As a result of considerable investigation aimed at achieving the above object, the inventors of the present invention were able to complete the present invention, including the aspects described below.

[1] A method for producing a disulfonylamine alkali metal salt, including:

a step of subjecting a disulfonylamine onium salt represented by formula [I] to a cation exchange reaction in an organic solvent, thereby producing a disulfonylamine alkali metal salt represented by formula [II] (hereafter sometimes referred to as the disulfonylamine alkali metal salt [II]), and a step of filtering the organic solvent solution containing the disulfonylamine alkali metal salt through a filter having a particle retention size of 0.1 to 10 μm to obtain a filtrate.

[Chemical Formula 1]

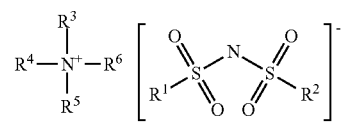

[I]

In formula [I], each of $R^1$ and $R^2$ independently represents a fluorine atom or a fluorinated alkyl group having 1 to 6 carbon atoms, provided that at least one of $R^1$ and $R^2$ represents a fluorine atom.

Each of $R^3$, $R^4$, $R^5$ and $R^6$ independently represents a hydrogen atom, an alkyl group having 1 to 6 carbon atoms, or an alkoxyalkyl group having 1 to 6 carbon atoms, and two groups among $R^3$, $R^4$, $R^5$ and $R^6$ may be combined to form a 5- to 8-membered ring in which the nitrogen atom to which the groups are bonded functions as one of the ring atoms.

[Chemical Formula 2]

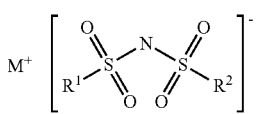

[II]

In formula [II], $M^+$ represents an alkali metal cation, and $R^1$ and $R^2$ are as defined in formula [I].

[2] The method disclosed in [1], wherein the filter is a membrane filter.

[3] The method disclosed in [1] or [2], wherein the organic solvent is an ester-based solvent.

[4] The method disclosed in [1] or [2], wherein the organic solvent is isopropyl acetate.

[5] The method disclosed in any one of [1] to [4], further including, after the filtering step, a step of concentrating the filtrate at a temperature of 0 to 70° C.

[6] The method disclosed in [5], wherein after the filtering step, the filtrate is concentrated at a temperature of 0 to 50° C.

[7] The method disclosed in any one of [1] to [6], further including, after the step of performing the cation exchange reaction and before the filtering step, a step of removing onium cations from the organic solvent solution by washing the organic solvent solution with water.

[8] The method disclosed in any one of [5] to [7], further including, after the concentration step, a step of precipitating the disulfonylamine alkali metal salt.

Effects of the Invention

According to the present invention, a high-purity disulfonylamine alkali metal salt [II] can be produced with a low temperature history and at low cost.

BEST MODE FOR CARRYING OUT THE INVENTION

The method for producing a disulfonylamine alkali metal salt according to the present invention includes a step of subjecting a disulfonylamine onium salt to a cation exchange reaction in an organic solvent, thereby producing a disulfonylamine alkali metal salt [II], and a step of filtering the organic solvent solution containing the disulfonylamine alkali metal salt through a filter to obtain a filtrate.

The disulfonylamine onium salt used in the present invention is a compound represented by formula [I] (hereafter sometimes referred to as the disulfonylamine onium salt [I]).

[Chemical Formula 3]

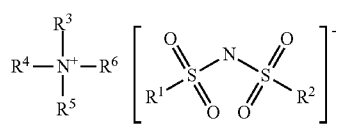

[I]

The disulfonylamine onium salt [I] is a salt formed from a disulfonylamine anion represented by formula [III] (hereafter sometimes referred to as the disulfonylamine anion [III]) and an onium cation represented by formula [IV] (hereafter sometimes referred to as the onium cation [IV]).

[Chemical Formula 4]

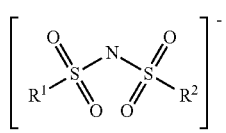

[III]

[Chemical Formula 5]

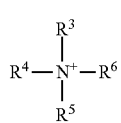

[IV]

In formula [III], each of $R^1$ and $R^2$ independently represents a fluorine atom or a fluorinated alkyl group having 1 to 6 carbon atoms, provided that at least one of $R^1$ and $R^2$ represents a fluorine atom.

The number of carbon atoms that constitute the fluorinated alkyl group of $R^1$ or $R^2$ is typically from 1 to 6, preferably from 1 to 4, and more preferably 1 or 2. Examples of the fluorinated alkyl group include a fluoromethyl group, difluoromethyl group, trifluoromethyl group, fluoroethyl group, difluoroethyl group, 2,2,2-trifluoroethyl group, pentafluoroethyl group, 3,3,3-trifluoropropyl group, perfluoro-n-propyl group, fluoropropyl group, perfluoroisopropyl group, fluorobutyl group, 3,3,4,4,4-pentafluorobutyl group, perfluoro-n-butyl group, perfluoroisobutyl group, perfluoro-t-butyl group, perfluoro-sec-butyl group, fluoropentyl group, perfluoropentyl group, perfluoroisopentyl group, perfluoro-t-pentyl group, fluorohexyl group, perfluoro-n-hexyl group and perfluoroisohexyl group. Among these groups, a trifluoromethyl group, pentafluoroethyl group or perfluoro-n-propyl group is preferable, and a trifluoromethyl group or pentafluoroethyl group is more preferable.

Specific examples of the disulfonylamine anion [III] include a bis(fluorosulfonyl)amine anion, an N-(fluorosulfonyl)-N-(trifluoromethylsulfonyl)amine anion, and an N-(fluorosulfonyl)-N-(pentafluoroethylsulfonyl)amine anion. Among these, a bis(fluorosulfonyl)amine anion in which $R^1$ and $R^2$ are both fluorine atoms is preferable.

In formula [IV], each of $R^3$, $R^4$, $R^5$ and $R^6$ independently represents a hydrogen atom, an alkyl group having 1 to 6 carbon atoms, or an alkoxyalkyl group having 1 to 6 carbon atoms, and two groups among $R^3$, $R^4$, $R^5$ and $R^6$ may be combined to form a 5- to 8-membered ring in which the nitrogen atom to which the groups are bonded functions as one of the ring atoms.

In formula [IV], the number of carbon atoms that constitute the alkyl group of $R^3$, $R^4$, $R^5$ or $R^6$ is typically from 1 to 6, preferably from 1 to 4, and more preferably 1 or 2. Examples of the alkyl group include a methyl group, ethyl group, n-propyl group, isopropyl group, n-butyl group, sec-butyl group, t-butyl group, pentyl group, isopentyl group, t-pentyl group, hexyl group and isohexyl group. Among these groups, a methyl group, ethyl group or propyl group is preferable.

In formula [IV], the number of carbon atoms that constitute the alkoxyalkyl group of $R^3$, $R^4$, $R^5$ or $R^6$ is typically from 2 to 6, preferably from 2 to 4, and more preferably 2 or 3. Examples of the alkoxyalkyl group include a methoxymethyl group, ethoxymethyl group, isopropoxymethyl group, t-butoxymethyl group, propoxymethyl group, butoxymethyl group, 2-methoxyethyl group, 2-ethoxyethyl group, 2-isopropoxyethyl group, 2-methoxypropyl group, 2-t-butoxyethyl group, and 2-propoxyethyl group. Among these groups, a methoxymethyl group, ethoxymethyl group or ethoxyethyl group is preferable.

Specific examples of the onium cation [IV] include an ammonium cation, dimethylammonium cation, trimethylammonium cation, tetramethylammonium cation, diethylammonium cation, triethylammonium cation, tetraethylammonium cation, tetrabutylammonium cation, pyrrolidinium cation, piperidinium cation, 4-morpholinium cation, 1,1-dimethylpyrrolidinium cation, 1,1-dimethylpiperidinium cation, 1-ethyl-1-methylpyrrolidinium cation, 1-ethyl-1-methylpiperidinium cation, 1-methyl-1-propylpyrrolidinium cation, 1-methyl-1-propylpiperidinium cation, 1-(methoxymethyl)-1-methylpyrrolidinium cation, and 1-(methoxymethyl)-1-methylpiperidinium cation. Among these, an ammonium cation in which $R^3$, $R^4$, $R^5$ and $R^6$ are all hydrogen atoms is preferable.

In the disulfonylamine onium salt [I], there are no particular limitations on the molar ratio between the disulfonylamine anion [III] and the onium cation [IV]. Because the disulfonylamine anion [III] is a monovalent anion and the onium cation [IV] is a monovalent cation, the molar ratio is usually 1:1.

There are no particular limitations on the method used for obtaining the disulfonylamine onium salt [I]. The disulfonylamine onium salt [I] may be a commercially available product, or may be produced using a known method such as that disclosed in JP 2010-168249 A.

Specific examples of the disulfonylamine onium salt [I] include ammonium bis(fluorosulfonyl)amine, ammonium N-(fluorosulfonyl)-N-(trifluoromethylsulfonyl)amine, ammonium N-(fluorosulfonyl)-N-(pentafluoroethylsulfonyl)amine, dimethylammonium bis(fluorosulfonyl)amine, dimethylammonium N-(fluorosulfonyl)-N-(trifluoromethylsulfonyl)amine, dimethylammonium N-(fluorosulfonyl)-N-(pentafluoroethylsulfonyl)amine, trimethylammonium bis(fluorosulfonyl)amine, trimethylammonium N-(fluorosulfonyl)-N-(trifluoromethylsulfonyl)amine, trimethylammonium N-(fluorosulfonyl)-N-(pentafluoroethylsulfonyl)amine, tetramethylammonium bis(fluorosulfonyl)amine, tetramethylammonium N-(fluorosulfonyl)-N-(trifluoromethylsulfonyl)amine, tetramethylammonium N-(fluorosulfonyl)-N-(pentafluoroethylsulfonyl)amine, diethylammonium bis(fluorosulfonyl)amine, diethylammonium N-(fluorosulfonyl)-N-(trifluoromethylsulfonyl)amine, diethylammonium N-(fluorosulfonyl)-N-(pentafluoroethylsulfonyl)amine, triethylammonium bis(fluorosulfonyl)amine, triethylammonium N-(fluorosulfonyl)-N-(trifluoromethylsulfonyl)amine, triethylammonium N-(fluorosulfonyl)-N-(pentafluoroethylsulfonyl)amine, tetraethylammonium bis(fluorosulfonyl)amine, tetraethylammonium N-(fluorosulfonyl)-N-(trifluoromethylsulfonyl)amine, tetraethylammonium N-(fluorosulfonyl)-N-(pentafluoroethylsulfonyl)amine, tetrabutylammonium bis(fluorosulfonyl)amine, tetrabutylammonium N-(fluorosulfonyl)-N-(trifluoromethylsulfonyl)amine, tetrabutylammonium N-(fluorosulfonyl)-N-(pentafluoroethylsulfonyl)amine, pyrrolidinium bis(fluorosulfonyl)amine, pyrrolidinium N-(fluorosulfonyl)-N-(trifluoromethylsulfonyl)amine, pyrrolidinium N-(fluorosulfonyl)-N-(pentafluoroethylsulfonyl)amine, piperidinium bis(fluorosulfonyl)amine, piperidinium N-(fluorosulfonyl)-N-(trifluoromethylsulfonyl)amine, piperidinium N-(fluorosulfonyl)-N-(pentafluoroethylsulfonyl)amine, 4-morpholinium bis(fluorosulfonyl)amine, 4-morpholinium N-(fluorosulfonyl)-N-(trifluoromethylsulfonyl)amine, 4-morpholinium N-(fluorosulfonyl)-N-(pentafluoroethylsulfonyl)amine, 1,1-dimethylpyrrolidinium bis(fluorosulfonyl)amine, 1,1-dimethylpyrrolidinium N-(fluorosulfonyl)-N-(trifluoromethylsulfonyl)amine, 1,1-dimethylpyrrolidinium N-(fluorosulfonyl)-N-(pentafluoroethylsulfonyl)amine, 1,1-dimethylpiperidinium bis(fluorosulfonyl)amine, 1,1-dimethylpiperidinium N-(fluorosulfonyl)-N-(trifluoromethylsulfonyl)amine, 1,1-dimethylpiperidinium N-(fluorosulfonyl)-N-(pentafluoroethylsulfonyl)amine, 1-ethyl-1-methylpyrrolidinium bis(fluorosulfonyl)amine, 1-ethyl-1-methylpyrrolidinium N-(fluorosulfonyl)-N-(trifluoromethylsulfonyl)amine, 1-ethyl-1-methylpyrrolidinium N-(fluorosulfonyl)-N-(pentafluoroethylsulfonyl)amine, 1-ethyl-1-methylpiperidinium bis(fluorosulfonyl)amine, 1-ethyl-1-methylpiperidinium N-(fluorosulfonyl)-N-(trifluoromethylsulfonyl)amine, 1-ethyl-1-methylpiperidinium N-(fluorosulfonyl)-N-(pentafluoroethylsulfonyl)amine, 1-methyl-1-propylpyrrolidinium bis(fluorosulfonyl)amine, 1-methyl-1-propylpyrrolidinium N-(fluorosulfonyl)-N-(trifluoromethylsulfonyl)amine, 1-methyl-1-propylpyrrolidinium N-(fluorosulfonyl)-N-(pentafluoroethylsulfonyl)amine, 1-methyl-1-propylpiperidinium bis(fluorosulfonyl)amine, 1-methyl-1-propylpiperidinium N-(fluorosulfonyl)-N-(trifluoromethylsulfonyl)amine, 1-methyl-1-propylpiperidinium N-(fluorosulfonyl)-N-(pentafluoroethylsulfonyl)amine, 1-(methoxymethyl)-1-methylpyrrolidinium bis(fluorosulfonyl)amine, 1-(methoxymethyl)-1-methylpyrrolidinium N-(fluorosulfonyl)-N-(trifluoromethylsulfonyl)amine, 1-(methoxymethyl)-1-methylpyrrolidinium N-(fluorosulfonyl)-N-(pentafluoroethylsulfonyl)amine, 1-(methoxymethyl)-1-methylpiperidinium bis(fluorosulfonyl)amine, 1-(methoxymethyl)-1-methylpiperidinium N-(fluorosulfonyl)-N-(trifluoromethylsulfonyl)amine, and 1-(methoxymethyl)-1-methylpiperidinium N-(fluorosulfonyl)-N-(pentafluoroethylsulfonyl)amine Among these salts, ammonium bis(fluorosulfonyl)amine is preferable.

There are no particular limitations on the organic solvent used in the production method of the present invention, but a solvent that is capable of dissolving the disulfonylamine onium salt and the disulfonylamine alkali metal salt is preferable. Examples of preferred organic solvents include aprotic solvents such as ethylene carbonate, propylene carbonate, butylene carbonate, γ-butyrolactone, γ-valerolactone, dimethoxymethane, 1,2-dimethoxyethane, tetrahydrofuran, 2-methyltetrahydrofuran, 1,3-dioxane, 4-methyl-1,3-dioxolane, methyl formate, methyl acetate, methyl propionate, dimethyl carbonate, ethyl methyl carbonate, diethyl carbonate, sulfolane, 3-methylsulfolane, dimethylsulfoxide, N,N-dimethylformamide, N-methyloxazolidinone, acetonitrile, valeronitrile, benzonitrile, ethyl acetate, isopropyl acetate, butyl acetate, nitromethane and nitrobenzene. Among these solvents, from the viewpoint of obtaining a higher purity disulfonylamine alkali metal salt [II], an ester-based solvent such as ethyl acetate, isopropyl acetate or butyl acetate is preferable, and isopropyl acetate is particularly desirable. From the viewpoint of enabling the temperature to be lowered during concentration of the filtrate after the filtering step, isopropyl acetate is particularly preferred among the ester-based solvents.

In the present invention, an alkali metal compound is used in the cation exchange reaction. Examples of the alkali metal compound include hydroxides such as LiOH, NaOH, KOH, RbOH and CsOH, carbonates such as $Li_2CO_3$, $Na_2CO_3$, $K_2CO_3$, $Rb_2CO_3$ and $Cs_2CO_3$, hydrogen carbonates such as $LiHCO_3$, $NaHCO_3$, $KHCO_3$, $RbHCO_3$ and $CsHCO_3$, chlorides such as LiCl, NaCl, KCl, RbCl and CsCl, bromides such as LiBr, NaBr, KBr, RbBr and CsBr, fluorides such as LiF, NaF, KF, RbF and CsF, alkoxide compounds such as $CH_3OLi$, EtOLi, t-BuOK and t-BuONa, hydrides such as NaH, KH and LiH, and alkyllithium compounds such as i-$Pr_2NLi$, EtLi, BuLi and t-BuLi (wherein Et represents an ethyl group, Pr represents a propyl group and Bu represents a butyl group). Of these compounds, a hydroxide such as LiOH, NaOH, KOH, RbOH or CsOH is preferable.

The amount used of the alkali metal compound is preferably from 1 mol to 10 mol, and more preferably from 1 mol to 5 mol, per 1 mol of the disulfonylamine onium salt [I].

The cation exchange reaction can be conducted, for example, by mixing the disulfonylamine onium salt [I] and the alkali metal compound in the organic solvent. There are no particular limitations on the temperature during the cation exchange reaction, but the temperature is preferably from 0° C. to 200° C., and more preferably from 10° C. to 100° C. The time required for the reaction varies depending on the reaction scale, but is preferably from 0.1 hours to 48 hours, and more preferably from 0.5 hours to 24 hours.

In the present invention, this step of performing a cation exchange reaction converts the disulfonylamine onium salt [I] into a disulfonylamine alkali metal salt represented by formula [II].

[Chemical Formula 6]

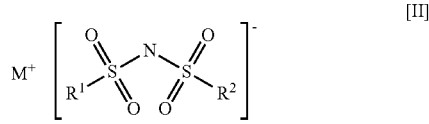

In formula [II], $M^+$ represents an alkali metal cation, and $R^1$ and $R^2$ are as defined in formula [I]. The disulfonylamine alkali metal salt [II] is a salt formed from the aforementioned disulfonylamine anion [III] and the alkali metal cation M.

Examples of the alkali metal cation include a lithium cation, sodium cation, potassium cation and cesium cation.

In the disulfonylamine alkali metal salt [II], there are no particular limitations on the molar ratio between the disulfonylamine anion [III] and the alkali metal cation M. Because the disulfonylamine anion [III] is a monovalent anion and the alkali metal cation $M^+$ is a monovalent cation, the molar ratio is usually 1:1.

Specific examples of the disulfonylamine alkali metal salt [II] include lithium bis(fluorosulfonyl)amine, lithium N-(fluorosulfonyl)-N-(trifluoromethylsulfonyl)amine, lithium N-(fluorosulfonyl)-N-(pentafluoroethylsulfonyl)amine, sodium bis(fluorosulfonyl)amine, sodium N-(fluorosulfonyl)-N-(trifluoromethylsulfonyl)amine, sodium N-(fluorosulfonyl)-N-(pentafluoroethylsulfonyl)amine, potassium bis(fluorosulfonyl)amine, potassium N-(fluorosulfonyl)-N-(trifluoromethylsulfonyl)amine, potassium N-(fluorosulfonyl)-N-(pentafluoroethylsulfonyl)amine, cesium bis(fluorosulfonyl)amine, cesium N-(fluorosulfonyl)-N-(trifluoromethylsulfonyl)amine, and cesium N-(fluorosulfonyl)-N-(pentafluoroethylsulfonyl)amine.

In the production method of the present invention, prior to the filtering step described below, the organic solvent solution containing the disulfonylamine alkali metal salt [II] obtained as a result of the above cation exchange reaction is preferably washed with water to remove the onium cations from the organic solvent solution. There are no particular limitations on the washing method, and for example the washing may be performed by adding water to the organic solvent solution, performing thorough mixing, leaving the mixed liquid to stand and separate into an organic solvent phase and a water phase, and then separating and removing the water phase. This extraction operation may be performed using a batch method or a continuous method.

Subsequently, in the production method of the present invention, the organic solvent solution containing the disulfonylamine alkali metal salt [II] is filtered through a filter. The organic solvent solution may be the solution obtained immediately after the cation exchange reaction, the solution obtained following extraction with water, or a solution obtained by using a conventional method to adjust the concentration of either of these solutions to a concentration described below.

Examples of the filter used in the present invention include a flat filter paper, extraction thimble, cartridge filter, capsule filter, membrane filter, hollow membrane filter, pleated membrane filter, or a filter packed with a filter medium such as a non-woven cloth, cellulose, activated carbon or diatomaceous earth. Among these, a membrane filter is preferable. The filter medium of the membrane filter, hollow membrane filter or pleated membrane filter is preferably composed of a polyolefin such as ultra high density polyethylene or polypropylene, a fluororesin such as PTFE, nylon, a cellulose resin, glass fiber, stainless steel fiber, silica fiber, a polycarbonate, cotton, a polyether sulfone, or a cellulose acetate or the like. Further, the filter may also contain an ion exchange material such as a cation exchange resin, or a cation charge regulator that generates a zeta potential in the organic solvent solution being filtered.

The filter used in the production method of the present invention has a particle retention size that is preferably from 0.1 to 10 µm, and more preferably from 0.1 to 5 µm. By performing filtering with a filter having a particle retention size within this type of range, very fine impurities can be removed, and a high-purity disulfonylamine alkali metal salt [II] can be obtained. If the particle retention size is too small, then the filter tends to be prone to blockages. In contrast, if the particle retention size is too large, then the ability to remove very fine impurities tends to be poor.

In the present invention, after the filtering step described above, the filtrate is preferably concentrated at a temperature of 0 to 70° C., and more preferably concentrated at a temperature of 0 to 50° C. The concentration operation is preferably conducted under reduced pressure. By limiting the liquid temperature to 0 to 50° C. during the concentration process, an organic solvent solution of a high-purity disulfonylamine alkali metal salt [II] can be obtained which contains no impurities generated as a result of thermal degradation. After the concentration step, the disulfonylamine alkali metal salt [II] is preferably precipitated.

In this manner, the disulfonylamine alkali metal salt [II] obtained by executing the production method of the present invention contains dramatically reduced amounts of impurities, and particularly chloride ions, fluoride ions and sulfate ions. The high-purity disulfonylamine alkali metal salt [II] obtained using the production method of the present invention can be used favorably as the material for an ion conductor used in producing an electrochemical device such as a lithium ion secondary cell.

EXAMPLES

The present invention is described below in further detail using a series of examples. However, the present invention is in no way limited by the following examples, and appropriate modifications can, of course, be made while still conforming with the purport of the present invention, with all such modifications deemed to be included within the technical scope of the present invention.

Synthesis Example 1 (Synthesis of Ammonium Di(Fluorosulfonyl)Amine)

A fluororesin reaction vessel was charged with 2.14 parts by mass of di(chlorosulfonyl)amine, 17.6 parts by mass of butyl acetate and 1.78 parts by mass of $NH_4F$ were added, and the resulting mixture was reacted under reflux at 75° C. for 4 hours. Following completion of the reaction, the reaction mixture was cooled to room temperature, and 2.5 parts by mass of water was added to extract the water-soluble components. The water phase was removed and discarded, and the organic phase was concentrated, yielding ammonium di(fluorosulfonyl)amine.

Example 1 (Synthesis of Lithium Di(Fluorosulfonyl)Amine (Hereafter Referred to as LFSI))

To 19.8 g (0.10 mol) of the ammonium di(fluorosulfonyl) amine obtained in Synthesis Example 1 were added 60 mL of isopropyl acetate and 5.5 g (0.13 mol) of lithium hydroxide monohydrate, and the resulting mixture was heated under reflux at an absolute pressure of 9.333 kPa and a temperature of 27° C. to 33° C. for a period of 1.5 hours. The thus obtained liquid was cooled to 25° C., 50 ml of isopropyl acetate and 20 ml of water were added, and an extraction was performed. The organic phase and the water phase were separated, and then 50 ml of isopropyl acetate was added to the water phase to extract the water-insoluble components. The organic phases obtained from the above extraction operations were combined and mixed, and then three extractions were performed with 5 ml samples of water to remove any water-soluble components. The resulting organic phase was placed in a reaction vessel fitted with a Dean Stark apparatus, and refluxed under reduced pressure at a temperature of 35° C. and an absolute pressure of about 13.33 kPa for 3.5 hours, while an additional 130 ml of isopropyl acetate was added to the reaction vessel, thereby removing the moisture from the solution. The thus obtained organic solvent solution was then filtered through a membrane filter having a particle retention size of 1.0 μm. The filtrate was placed in a rotary evaporator, and solvent evaporation at 40° C. was performed to concentrate the solution down to an LFSI concentration of 57.9% by mass. Next, 160 ml of methylene chloride was added dropwise to the concentrated LFSI solution, thereby precipitating crystals. The crystals were collected by filtration under reduced pressure. The filtered crystals were washed with 45 ml of methylene chloride and then dried under vacuum at room temperature for 8 hours, yielding 4.58 g of LFSI. The thus obtained LFSI had a $F^-$ content of less than 5 ppm, a $Cl^-$ content of less than 5 ppm, and a $SO_4^{2-}$ content of less than 5 ppm.

Comparative Example 1 (Synthesis of LFSI)

To 19.8 g (0.10 mol) of the ammonium di(fluorosulfonyl) amine obtained in Synthesis Example 1 were added 60 mL of isopropyl acetate and 5.5 g (0.13 mol) of lithium hydroxide monohydrate, and the resulting mixture was heated under reflux at an absolute pressure of 9.333 kPa and a temperature of 27° C. to 34° C. for a period of 1.5 hours. The thus obtained liquid was cooled to 25° C., 50 ml of isopropyl acetate and 26 ml of water were added, and an extraction was performed. The organic phase and the water phase were separated, and then 50 ml of isopropyl acetate was added to the water phase to extract the water-insoluble components. The organic phases obtained from the above extraction operations were combined and mixed, and then three extractions were performed with 5 ml samples of water to remove any water-soluble components. The resulting organic phase was placed in a reaction vessel fitted with a Dean Stark apparatus, and refluxed under reduced pressure at a temperature of 35° C. and an absolute pressure of about 7.99 kPa for 5 hours, thereby removing the moisture from the solution. The thus obtained organic solvent solution was placed in a rotary evaporator, and solvent evaporation at 40° C. was performed to concentrate the solution down to an LFSI concentration of 54.4% by mass. Next, 180 ml of methylene chloride was added dropwise to the concentrated LFSI solution, thereby precipitating crystals. The crystals were collected by filtration under reduced pressure. The filtered crystals were washed with 90 ml of methylene chloride and then dried under vacuum at room temperature for 8 hours, yielding 4.41 g of LFSI. The thus obtained LFSI had a $F^-$ content of 46 ppm, a $Cl^-$ content of less than 5 ppm, and a $SO_4^{2-}$ content of 10 ppm.

Example 2 (Synthesis of LFSI)

To 19.8 g (0.10 mol) of the ammonium di(fluorosulfonyl) amine obtained in Synthesis Example 1 were added 100 mL of isopropyl acetate and 5.5 g (0.13 mol) of lithium hydroxide monohydrate, and the resulting mixture was heated under reflux at an absolute pressure of 9.333 kPa and a temperature of 27° C. to 33° C. for a period of 1.5 hours. The thus obtained liquid was cooled to 25° C., 20 ml of water was added, and an extraction was performed. The organic phase and the water phase were separated, and then 50 ml of isopropyl acetate was added to the water phase to extract the water-insoluble components. The organic phases obtained from the above extraction operations were combined and mixed, and then three extractions were performed with 5 ml samples of water to remove any water-soluble components. The resulting organic phase was placed in a reaction vessel fitted with a Dean Stark apparatus, and refluxed under reduced pressure at a temperature of 35° C. and an absolute pressure of 10.66 to 13.33 kPa for 5 hours, thereby removing the moisture from the solution. The thus obtained organic solvent solution was filtered through a Kiriyama No. 5B filter (particle retention size: 4 μm). Subsequently, 41.9 g of the 75.2 g of obtained LFSI solution was placed in a rotary evaporator, and solvent evaporation at 40° C. was performed to concentrate the solution down to an LFSI concentration of 56.4% by mass. Next, 100 ml of methylene chloride was added dropwise to the concentrated LFSI solution, thereby precipitating crystals. The crystals were collected by filtration under reduced pressure. The filtered crystals were washed with 45 ml of methylene chloride and then dried under vacuum at room temperature for 8 hours, yielding 2.69 g of LFSI. The thus obtained LFSI had a $F^-$ content of less than 5 ppm, a $Cl^-$ content of 6 ppm, and a $SO_4^{2-}$ content of 6 ppm.

Example 3 (Synthesis of LFSI)

To 19.8 g (0.10 mol) of the ammonium di(fluorosulfonyl) amine obtained in Synthesis Example 1 were added 100 mL of isopropyl acetate and 5.5 g (0.13 mol) of lithium hydroxide monohydrate, and the resulting mixture was heated under reflux at an absolute pressure of 9.333 kPa and a temperature of 27° C. to 33° C. for a period of 1.5 hours. The thus obtained liquid was cooled to 25° C., 20 ml of water were added, and an extraction was performed. The organic phase and the water phase were separated, and then 50 ml of isopropyl acetate was added to the water phase to extract the water-insoluble components. The organic phases obtained from the above extraction operations were combined and mixed, and then three extractions were performed with 5 ml samples of water to remove any water-soluble components. The resulting organic phase was placed in a reaction vessel fitted with a Dean Stark apparatus, and refluxed under reduced pressure at a temperature of 35° C. and an absolute pressure of 10.66 to 13.33 kPa for 5 hours, thereby removing the moisture from the solution. The thus obtained organic solvent solution was then filtered through a Kiriyama No. 5B filter (particle retention size: 4 μm). Subsequently, 33.3 g of the 75.2 g of obtained LFSI solution was placed in a rotary evaporator, and solvent evaporation at 60° C. was performed to concentrate the solution down to an LFSI concentration of 67.4% by mass. Next, 80 ml of methylene chloride was added dropwise to the concentrated LFSI solution, thereby precipitating crystals. The crystals were collected by filtration under reduced pressure. The filtered crystals were washed with 45 ml of methylene chloride and then dried under vacuum at room temperature for 8 hours, yielding 5.00 g of LFSI. The thus obtained LFSI had a F$^-$ content of 66 ppm, a Cl$^-$ content of less than 5 ppm, and a SO$_4^{2-}$ content of 76 ppm.

Comparative Example 2 (Synthesis of LFSI)

To 1306.6 g of a butyl acetate solution containing 356.7 g (1.80 mol) of the ammonium di(fluorosulfonyl)amine obtained in Synthesis Example 1 was added 98.2 g (2.34 mol) of lithium hydroxide monohydrate, and the resulting mixture was heated under reflux at an absolute pressure of 8.67 kPa and a temperature of 31° C. to 35° C. for a period of 4 hours. The thus obtained liquid was cooled to 25° C., 182 ml of water was added, and an extraction was performed. The organic phase and the water phase were separated, and then 900 ml of butyl acetate was added to the water phase to extract the water-insoluble components. The organic phases obtained from the above extraction operations were combined and mixed, and then four extractions were performed with 20 ml samples of water to remove any water-soluble components. The thus obtained organic solvent solution was placed in a rotary evaporator, and solvent evaporation at 60° C. was performed to concentrate the solution down to an LFSI concentration of 56.9% by mass. Next, 1,450 ml of methylene chloride was added dropwise to the concentrated LFSI solution, thereby precipitating crystals. The crystals were collected by filtration under reduced pressure. The filtered crystals were washed with 600 ml of methylene chloride and then dried under vacuum at room temperature for 9 hours, yielding 114.8 g of LFSI. The thus obtained LFSI had a F$^-$ content of 288 ppm, a Cl$^-$ content of 10 ppm, and a SO$_4^{2-}$ content of 49 ppm.

Example 4 (Synthesis of LFSI)

To 153.2 g of a butyl acetate solution containing 41.8 g (0.2 mol) of the ammonium di(fluorosulfonyl)amine obtained in Synthesis Example 1 was added 15.9 g (0.36 mol) of lithium hydroxide monohydrate, and the resulting mixture was heated under reflux at an absolute pressure of 5.33 kPa and a temperature of 31° C. to 32° C. for a period of 4 hours. The thus obtained liquid was filtered through a Kiriyama No. 5B filter (particle retention size: 4 μm), thereby removing any insoluble components (such as LiOH). Next, 100 ml of butyl acetate and 30 ml of water were added to the resulting filtrate, and an extraction was performed. The organic phase and the water phase were separated, and the organic phase was subjected to two extractions with 10 ml samples of water to remove any water-soluble components. The organic phase was then placed in a rotary evaporator, and concentrated down to an LFSI concentration of 58.8% by mass at 60° C. Next, 160 ml of methylene chloride was added dropwise to the concentrated LFSI solution, thereby precipitating crystals. The crystals were collected by filtration under reduced pressure. The thus obtained crystals were washed with 320 ml of methylene chloride and then dried under vacuum at room temperature for 7 hours, yielding 14.96 g of LFSI. The thus obtained LFSI had a F$^-$ content of 11 ppm, a Cl$^-$ content of 11 ppm, and a SO$_4^{2-}$ content of 77 ppm.

It is evident that compared with Comparative Example 1 which lacked a filtering step, Examples 1 and 2 which included a filtering step yielded a disulfonylamine alkali metal salt of higher purity. Further, based on the results from Examples 2 and 3, it is evident that if, following the filtering step, the filtrate is concentrated at a temperature of 50° C. or lower, then a disulfonylamine alkali metal salt of higher purity is able to be obtained.

INDUSTRIAL APPLICABILITY

The present invention enables a high-purity disulfonylamine alkali metal salt [II] to be produced with a low temperature history and at low cost, and is therefore very useful industrially.

The invention claimed is:
1. A method for producing a disulfonylamine alkali metal salt, the method comprising:
a step of subjecting a disulfonylamine onium salt represented by formula [I]:

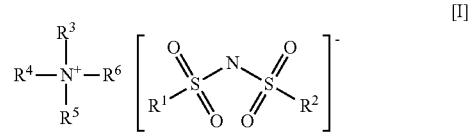

wherein each of R$^1$ and R$^2$ independently represents a fluorine atom, each of R$^3$, R$^4$, R$^5$ and R$^6$ independently represents a hydrogen atom, an alkyl group having 1 to 6 carbon atoms, or an alkoxyalkyl group having 1 to 6 carbon atoms, and two groups among R$^3$, R$^4$, R$^5$ and R$^6$ may be combined to form a 5- to 8-membered ring in which a nitrogen atom to which the groups are bonded functions as one of the ring atoms, to a cation exchange reaction in isopropyl acetate, thereby producing a disulfonylamine alkali metal salt represented by formula [II]:

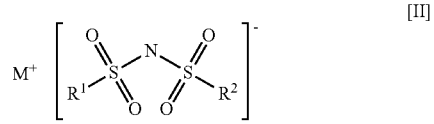

wherein M$^+$ represents an alkali metal cation, and R$^1$ and R$^2$ are as defined in formula [I];
a step of filtering an isopropyl acetate solution containing the disulfonylamine alkali metal salt through a filter having a particle retention size of 0.1 to 10 μm to obtain a filtrate;
after the filtering step, a step of concentrating the filtrate at a temperature of 0° C. or higher but lower than 50° C.; and
after the concentration step, a step of precipitating the disulfonylamine alkali metal salt.
2. The method according to claim 1, wherein the filter is a membrane filter.
3. The method according to claim 1, further comprising, after the step of performing the cation exchange reaction and before the filtering step, a step of removing onium cations from the isopropyl acetate solution by washing the isopropyl acetate solution with water.

\* \* \* \* \*